US008459101B2

(12) United States Patent
Stevenson

(10) Patent No.: US 8,459,101 B2
(45) Date of Patent: Jun. 11, 2013

(54) COMPOSITE CHROMATOGRAPHY COLUMN

(75) Inventor: John Victor Stevenson, Bel Air, MD (US)

(73) Assignee: Alltech Associates, Inc., Columbia, MD (US)

(*) Notice: Subject to any disclaimer, the term of this patent is extended or adjusted under 35 U.S.C. 154(b) by 662 days.

(21) Appl. No.: 11/992,904

(22) PCT Filed: Sep. 29, 2006

(86) PCT No.: PCT/US2006/038101
§ 371 (c)(1),
(2), (4) Date: Mar. 28, 2008

(87) PCT Pub. No.: WO2007/041315
PCT Pub. Date: Apr. 12, 2007

(65) Prior Publication Data
US 2009/0260420 A1  Oct. 22, 2009

Related U.S. Application Data

(60) Provisional application No. 60/722,059, filed on Sep. 29, 2005.

(51) Int. Cl.
*G01N 30/60* (2006.01)
*B01D 15/22* (2006.01)

(52) U.S. Cl.
USPC .................. 73/61.53; 210/198.2; 210/656

(58) Field of Classification Search
USPC ............................................. 73/23.39, 61.53
See application file for complete search history.

(56) References Cited

U.S. PATENT DOCUMENTS

| 3,727,451 | A | * | 4/1973 | Broerman ............... 73/23.39 |
| 4,070,285 | A | | 1/1978 | Abrahams |
| 4,280,905 | A | | 7/1981 | Gunkel et al. |
| 4,305,449 | A | | 12/1981 | Loszewski et al. |
| 4,357,305 | A | | 11/1982 | Loo |
| 4,417,459 | A | | 11/1983 | Tomita |
| 4,522,715 | A | | 6/1985 | Walters |
| 4,571,969 | A | | 2/1986 | Tomita |
| 4,655,384 | A | | 4/1987 | Rigdon et al. |
| 4,699,288 | A | | 10/1987 | Mohan |
| 4,769,141 | A | | 9/1988 | Couillard |
| 4,927,345 | A | | 5/1990 | Takei et al. |
| 4,971,742 | A | | 11/1990 | Brooks et al. |
| 4,971,846 | A | | 11/1990 | Lundy |
| 5,009,823 | A | | 4/1991 | Kromrey |
| 5,106,400 | A | | 4/1992 | Tick |
| 5,177,990 | A | | 1/1993 | Isgen |
| 5,253,778 | A | | 10/1993 | Sirosh |
| 5,436,042 | A | | 7/1995 | Lau et al. |
| 5,441,635 | A | * | 8/1995 | Ichitsuka et al. ........... 210/198.2 |
| 5,462,659 | A | | 10/1995 | Saxena et al. |
| 5,468,358 | A | | 11/1995 | Ohkawa et al. |

(Continued)

FOREIGN PATENT DOCUMENTS

| DE | 1169523 | 11/1969 |
| DE | 3432806 | 3/1986 |
| WO | 9521690 | 8/1995 |
| WO | 01/03797 | 1/2001 |

*Primary Examiner* — Daniel Larkin
(74) *Attorney, Agent, or Firm* — William D. Bunch

(57) ABSTRACT

Chromatography columns are disclosed. Methods of making chromatography columns and methods of using chromatography columns are also disclosed.

17 Claims, 3 Drawing Sheets

U.S. PATENT DOCUMENTS

| | | | |
|---|---|---|---|
| 5,494,188 A | 2/1996 | Sirosh | |
| 5,564,272 A | 10/1996 | Warner et al. | |
| 5,577,630 A | 11/1996 | Blair et al. | |
| 5,589,115 A | 12/1996 | Sherwood | |
| 5,651,886 A | 7/1997 | Hoffmann et al. | |
| 5,719,322 A * | 2/1998 | Lansbarkis et al. | 73/23.39 |
| 5,736,036 A * | 4/1998 | Upchurch et al. | 210/198.2 |
| 5,798,156 A | 8/1998 | Mitlitsky et al. | |
| 5,893,971 A | 4/1999 | Shalon et al. | |
| 5,936,861 A | 8/1999 | Jang et al. | |
| 5,951,873 A | 9/1999 | Shalon et al. | |
| 6,036,855 A | 3/2000 | Shalon et al. | |
| 6,425,172 B1 | 7/2002 | Rutz | |
| 6,460,721 B2 | 10/2002 | Bowen et al. | |
| 6,490,852 B1 * | 12/2002 | Mustacich et al. | 57/3 |
| 6,491,182 B1 | 12/2002 | Holroyd et al. | |
| 6,491,882 B1 | 12/2002 | VanDenBerg et al. | |
| 6,527,951 B1 | 3/2003 | Tuvim | |
| 6,651,307 B2 | 11/2003 | Portmann | |
| 6,797,174 B2 * | 9/2004 | Neuroth et al. | 210/656 |
| 6,802,966 B2 | 10/2004 | Wormsbecher | |
| 2003/0098279 A1 | 5/2003 | Cabrera et al. | |
| 2005/0006292 A1 * | 1/2005 | Horsman et al. | 210/198.2 |
| 2005/0155933 A1 | 7/2005 | Ma | |

* cited by examiner

COMPOSITE CHROMATOGRAPHY COLUMN

CROSS REFERENCE TO RELATED APPLICATION

This application is a continuation of U.S. Patent Application Ser. No. 60/722,059 filed Sep. 29, 2005.

FIELD OF THE INVENTION

The present invention is directed to chromatography columns, methods of making chromatography columns, and methods of using chromatography columns.

BACKGROUND OF THE INVENTION

There is a need in the art for chromatography columns that can withstand high pressure applications, and yet have a relatively low weight for handling purposes.

SUMMARY OF THE INVENTION

The present invention addresses some of the difficulties and problems discussed above by the discovery of new chromatography columns formed from fiber-reinforced materials. In one exemplary embodiment of the present invention, the chromatography column comprises a tubular wall structure having a first end, a second end, an inner wall surface facing an interior of the tubular wall structure, and an outer wall surface, wherein the tubular wall structure comprises a fiber-reinforced layer.

In a further exemplary embodiment of the present invention, the chromatography column comprises a column inlet at a first end of the column, wherein the column inlet has an inlet cross-sectional flow area; a column outlet at a second end of the column opposite the first end, wherein the column outlet having an outlet cross-sectional flow area; and a tubular wall structure extending between the column inlet and the column outlet, wherein the tubular wall structure (i) has a tubular cross-sectional flow area that is substantially constant along a length of the tubular wall structure and is substantially equal to the inlet cross-sectional flow area, the outlet cross-sectional flow area, or both, and (ii) comprises an outer fiber-reinforced layer, and an inner layer comprising a metal, ceramic, glass or polymer layer.

The present invention is also directed to methods of making chromatography columns. In one exemplary method, the method of making a chromatography column comprises forming a first sleeve comprising an inert material, and surrounding an outer surface of the first sleeve with a fiber-reinforced layer.

The present invention is further directed to methods of using chromatography columns. In one exemplary method of using a chromatography column, the method comprises a method of analyzing a test sample that potentially contains at least one analyte, wherein the method comprises the step of introducing the test sample into a chromatography column containing a rigid support media, wherein the rigid support media comprises a plurality of inorganic particles, organic particles, porous monoliths or other stationary phases used in chromatography and the chromatography column comprises a tubular wall structure comprising a fiber-reinforced layer.

These and other features and advantages of the present invention will become apparent after a review of the following detailed description of the disclosed embodiments and the appended claims.

DETAILED DESCRIPTION OF THE INVENTION

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

The present invention is directed to chromatography columns comprising a fiber-reinforced layer. The present invention is further directed to methods of making chromatography columns comprising a fiber-reinforced layer, as well as methods of using chromatography columns comprising a fiber-reinforced layer. One exemplary chromatography column of the present invention is shown in FIG. 1.

Figure 1:
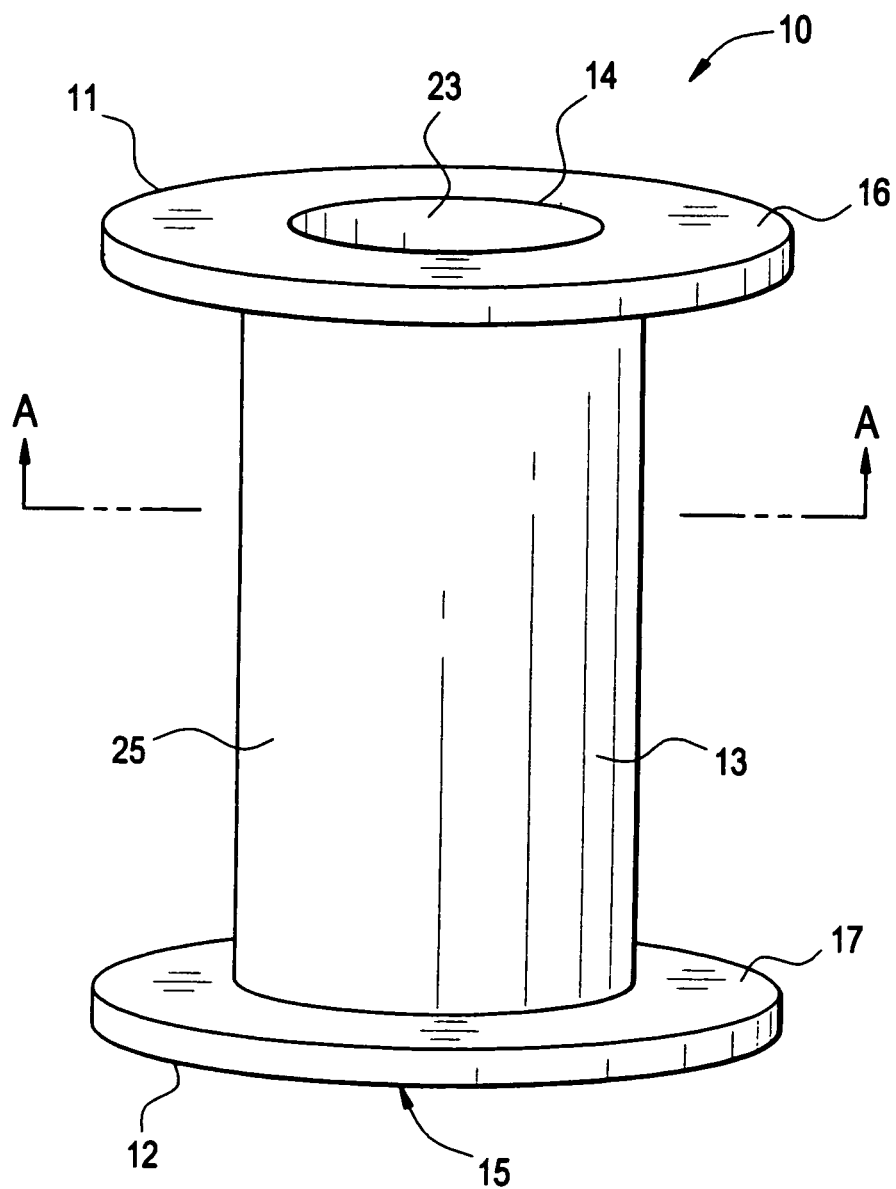
FIG. 1 depicts an exemplary chromatography column of the present invention.

As shown in FIG. 1, exemplary chromatography column 10 comprises a first end 11; a second end 12; a tubular wall structure 13 extending between first end 11 and second end 12; a column inlet 14 at first end 11; and a column outlet 15 at second end 12. Exemplary chromatography column 10 also comprises flanges 16 and 17 at first end 11 and second end 12 respectively. Flanges 16 and 17 may be used to connect exemplary chromatography column 10 to additional apparatus components at first end 11 and second end 12. A cross-sectional view of exemplary chromatography column 10 as viewed along line A-A in FIG. 1 is provided in FIG. 2.

Figure 2:
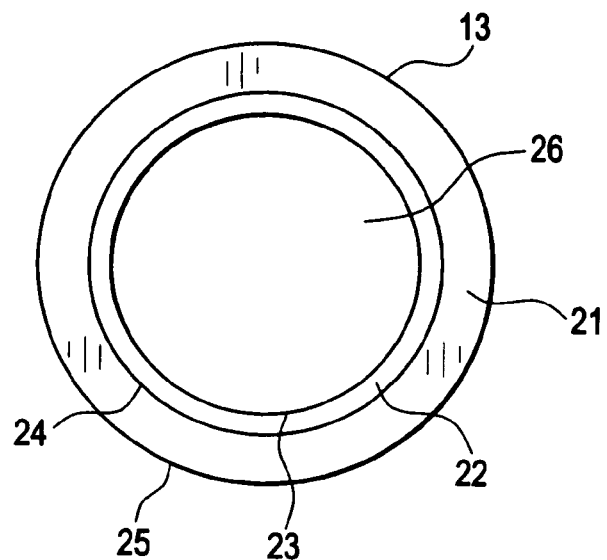
FIG. 2 depicts a cross-sectional view of the exemplary chromatography column shown in FIG. 1 along line A-A.

As shown in FIG. 2, tubular wall structure 13 of exemplary chromatography column 10 comprises two distinct layers: outer layer 21 forming an outer wall surface 25, and inner layer 22 forming an inner wall surface 23. In this exemplary embodiment, outer layer 21 and inner layer 22 are in direct contact with one another along intermediate surface 24. In one exemplary embodiment, outer layer 21 comprising a fiber-reinforced layer, while inner layer 22 comprises an inert material, such as aluminum, stainless steel, glass, ceramic or a polymeric material.

As shown in FIGS. 1-2, the chromatography columns of the present invention may comprise a number of components. A description of possible components and various configurations is provided below.

I. Chromatography Column Components and Configurations

The chromatography columns of the present invention may comprise one or more of the following components.

A. Chromatography Column Components

1. Tubular Wall Structure

The chromatography columns of the present invention comprise a tubular wall structure having one or more fiber-reinforced layers such as outer layer 21 of exemplary chromatography column 10 shown in FIGS. 1-2. The tubular wall structure may also comprise additional layers as discussed below.

a. Fiber-Reinforced Layers

The tubular wall structure comprises one or more fiber-reinforced layers. Each fiber-reinforced layer comprises fibers and a matrix material as described below.

i. Fibers

The tubular wall structure comprises one or more types of fibers. Suitable fibers for use in the fiber-reinforced layers include, but are not limited to, carbon tows (or fibers) (including graphite tows or fibers); aramid fibers, such as KEVLAR® and NOMEX® fibers; glass fibers including fiberglass fibers; polybenzoxazole (PBO) fibers; metal wire; quartz fibers; ceramic fibers; other polymeric yarns, fibers or filaments; or any combination thereof. The carbon tows may be polyacrylonitrile (PAN) or pitch derived carbon tows.

The fibers may be present as a single fiber or tow component, a fiber-containing layer, or multiple fiber-containing layers, wherein one or more layers contain continuous fibers and/or discontinuous fibers (e.g., staple length or chopped fibers having a fiber length of less than about 100 mm, typically less than about 10 mm). Suitable fiber-containing layers include, but are not limited to, woven fabrics, nonwoven fabrics, knitted fabrics, mesh materials, unidirectional arrays of fibers, or any combination thereof. Each fiber-containing layer may comprise one or more of the above-described types of fibers. In embodiments utilizing multiple fiber-containing layers, each of the fiber-containing layers may comprise one or more of the above-described types of fibers. Alternatively, in embodiments utilizing multiple fiber-containing layers, one or more fiber-containing layers may comprise a first type of fiber or fibers, while other fiber-containing layers may comprise a second type of fiber or fibers, wherein the second type of fiber or fibers differs from the first type of fiber or fibers.

In one embodiment of the present invention, the fibers are present as single fibers or tows within a matrix material that have been wound around a core (e.g., an inner sleeve), and subsequently cured (e.g., the matrix material comprises a thermosettable resin system) or hardened (e.g., the matrix material comprises a thermoplastic resin system).

In another embodiment, the fibers are present as woven fabrics or unidirectional arrays of fibers that have been positioned around a core (e.g., an inner sleeve) within a matrix material, and subsequently cured or hardened. In this embodiment, the woven fabrics or unidirectional arrays of fibers may be positioned so that the fibers are oriented in one or more directions relative to a length of the tubular wall structure. For example, the woven fabrics or unidirectional arrays of fibers may be positioned within the tubular wall structure so as to provide fibers oriented in one or more of the following directions relative to the length of the tubular wall structure: a 0° fiber orientation (i.e., fibers oriented in a direction along the length of the tubular wall structure), a 90° fiber orientation, a ±45° fiber orientation, a ±15° fiber orientation, or any combination thereof. Such fiber orientations are disclosed in U.S. Pat. No. 4,971,846, the subject matter of which is incorporated herein in its entirety.

A number of commercially available fibers may be used in the present invention. Suitable fibers include, but are not limited to, carbon tow or fibers designated T700, T100 or T800, which are commercially available from Toray Industries, Inc. (Tokyo, JP), and carbon tow or fibers designated IM7, which are commercially available from Hexcel Corporation (Stamford, Conn.); KEVLAR® fibers commercially available from DuPont (Wilmington, Del.); PBO fibers commercially available under the trade designation ZYLON® from Toyobo Company, Ltd. (Osaka, JP); and S-glass fibers commercially available from a number of fiber manufacturers including PPG Industries (Pittsburgh, Pa.). In one desired embodiment of the present invention, the fibers comprise T700SC carbon fibers from Toray Industries, Inc. (Tokyo, JP).

ii. Matrix Materials

The fibers may be embedded in a variety of matrix materials. Suitable matrix materials include, but are not limited to, thermoplastic resin materials, thermosettable resin materials, inorganic matrix materials including metals or metal oxides, ceramics, and carbon materials. In one exemplary embodiment, the fiber-reinforced layer comprises fibers embedded in a thermoplastic and/or thermosettable or thermoset resin material.

Suitable thermoplastic materials include, but are not limited to, polyamides such as nylon; polyolefins such as polypropylene; polystyrenes, acrylonitrile butadiene styrene (ABS) polymers; styrene acrylonitrile (SAN) polymers; polyethersulphones (PES); polyetherimides (PEI); polyphenylene sulphides (PPS); and polyaryletherketones (PEEK, PEK). Suitable thermosettable resin materials include, but are not limited to, epoxies, vinyl esters, polyesters, and phenolic resins.

Suitable inorganic matrix materials include, but are not limited to, metals or metal oxides, ceramics, and carbon materials. Suitable metal materials include, but are not limited to, metal and metal oxide materials disclosed in U.S. Pat. Nos. 5,936,861; 5,468,358; 4,655,384; and 4,305,449, the subject matter of all of which is incorporated herein in its entirety. Suitable ceramic materials include, but are not limited to, ceramic materials disclosed in U.S. Pat. Nos. 5,589,115 and 5,436,042, the subject matter of each of which is incorporated herein in its entirety. Suitable carbon matrix materials include, but are not limited to, carbon matrix materials disclosed in U.S. Pat. Nos. 5,009,823; 4,927,345; and 4,357,305, the subject matter of all of which is incorporated herein in its entirety.

In one desired embodiment of the present invention, the matrix material comprises a thermosettable or a thermoset epoxy resin. A number of commercially available epoxy resin systems may be used in the present invention. Suitable epoxy resin systems include, but are not limited to, epoxy resin systems HX1610-1, M21, and 8552 from Hexcel Corporation (Stamford, Conn.), and epoxy resin systems from Toray Industries, Inc. (Tokyo, JP). In one desired embodiment of the present invention, the matrix comprises a bisphenol-A epoxy resin system containing an anhydride hardener (e.g., hexahydro-4-methylpthalic anhydride (HMPA) or methyl tetrahydrophthalic anhydride (MTHPA)).

In one exemplary embodiment, the fiber-reinforced resin layers comprise prepregs containing a woven fabric or unidirectional array of fibers (e.g., carbon or graphite fibers or tow) within an epoxy resin matrix. In this embodiment, the epoxy resin may be a curable, B-staged epoxy resin, which may be further cured by applying additional heat and/or pressure. The prepregs may be wrapped around a preformed inner layer structure, and subsequently cured to a thermoset condition.

The fiber-reinforced layers of the present invention typically comprise from about 5 to about 95 percent by weight (pbw) of fibers, and from about 95 to 5 pbw of at least one matrix material, wherein the weight percentages are based on a total weight of the fiber-reinforced layer. More typically, the fiber-reinforced layers of the present invention comprise from about 40 to about 80 pbw of fibers, and from about 60 to about 20 pbw of at least one matrix material, wherein the weight percentages are based on a total weight of the fiber-reinforced layer. In one desired embodiment, the fiber-reinforced layers comprise about 60 pbw of fibers, and about 40 of at least one matrix material, such as an epoxy resin system, wherein the weight percentages are based on a total weight of the fiber-reinforced layer.

Each fiber-reinforced layer may have an average layer thickness that varies depending on the requirements of a given chromatography column (i.e., pressure capacity, diameter, height, etc.). Typically, each fiber-reinforced layer has an average layer thickness of from about 1.0 to about 50 millimeters (mm). In one desired embodiment, each fiber-reinforced layer has an average layer thickness of from about 1.0 to about 16 mm.

b. Other Layers

The tubular wall structure may comprise one or more layers in addition to the fiber-reinforced layers described above.

i. Inner Surface Layer

In one desired embodiment, the tubular wall structure comprises an inner surface layer. Typically, the inner surface layer comprises a material other than a fiber-reinforced layer, and more typically, comprises an inert material. Suitable inert materials include, but are not limited to, metals such as aluminum, stainless steel and titanium; polymeric materials such as polyetheretherketone (PEEK), and polytetrafluoroethylene (PTFE); glass including borosilicate glass; and ceramic materials. In one exemplary embodiment of the present invention, the inner surface layer comprises a metal selected from aluminum and stainless steel. In a further exemplary embodiment of the present invention, the inner surface layer comprises 6061-T6 aluminum or 316L stainless steel.

As with the fiber-reinforced layers described above, the inner surface layer may have an average layer thickness that varies depending on the requirements of a given chromatography column. Typically, the inner surface layer has an average layer thickness of from about 0.5 to about 50 millimeters (mm). In one desired embodiment, the inner surface layer has an average layer thickness of from about 1.0 to about 16 mm.

ii. Other Layers

The tubular wall structure may comprise one or more additional layers other than a fiber-reinforced layer and an inner surface layer. Other additional layers may include, but are not limited to, an outer wall surface coating layer; a tie layer (e.g., to enhance bonding) between a fiber-reinforced layer and any other layer; or a combination thereof. Suitable materials for forming additional layers include, but are not limited to, thermoplastic polymeric materials; thermosettable or thermoset materials such as an epoxy resin; an elastomeric material; any metal; glass; and ceramic materials. The additional layers may also be used to further increase the mechanical strength of the column tube.

In one exemplary embodiment, the tubular wall structure further comprises an outer wall glass layer. In this embodiment, the outer glass layer may be used to encapsulate a label, provide additional impact and abrasion resistance, or both. Typically, the outer glass layer has an average layer thickness of from about 0.1 to about 1.0 millimeters (mm).

In a further exemplary embodiment, the tubular wall structure may further comprise an outermost clear coat material applied over an outer surface of the tubular wall structure to provide enhanced chemical resistance. For example, the clear coat material may be applied over a fiber-reinforced layer, an outer wall glass layer, or any other outer layer. The clear coat material may comprise any clear coat material including, but not limited to, polyurethane materials. Typically, the clear coat layer has an average layer thickness of from about 0.01 to about 0.5 millimeters (mm).

Each additional layer may have an average layer thickness that varies depending on the purpose of the additional layer. Typically, each additional layer has an average layer thickness of from about 0.1 to about 250 millimeters (mm) depending on the type of additional layer (e.g., materials or composition), the function of the additional layer, and the location of the additional layer in the tubular wall structure.

2. Flanges

The chromatography columns of the present invention may comprise one or more flanges at either or both ends of the tubular wall structure such as flanges 16 and 17 of exemplary chromatography column 10 shown in FIGS. 1-2. Flanges may be used to connect the chromatography column to other components in a chromatography apparatus such as a seal, a filter, an end cap, etc.

In one embodiment of the present invention, flanges are formed as an integral part of one or more layers used to form the tubular wall structure. For example, in one embodiment of the present invention, flanges may be an extension of an inner layer of the tubular wall structure. Such a configuration is shown in exemplary chromatography column 10 shown in FIGS. 1-2. In other embodiments, a given flange may be an extension of an inner layer and an outer layer of the tubular wall structure.

In another embodiment of the present invention, flanges are an integral part of an end cap or other component that is separate from the tubular wall structure, and connectable to the tubular wall structure. In this embodiment, the end cap or other component may be joined to the tubular wall structure via mechanical fasteners such as corresponding sets of threads on an outer surface of the tubular wall structure and an inner surface of the end cap or other component. The flange may also be joined to one or more of the layers through adhesives or welds.

Each flange may further comprise one or more structural features to enable the flange to be connected to any other apparatus component. Suitable structural features include, but are not limited to, bolts extending from a surface of the flange, threaded holes within the flange, pipe threads, compression fittings, luer connectors, etc.

3. Separation Media

Figure 3:
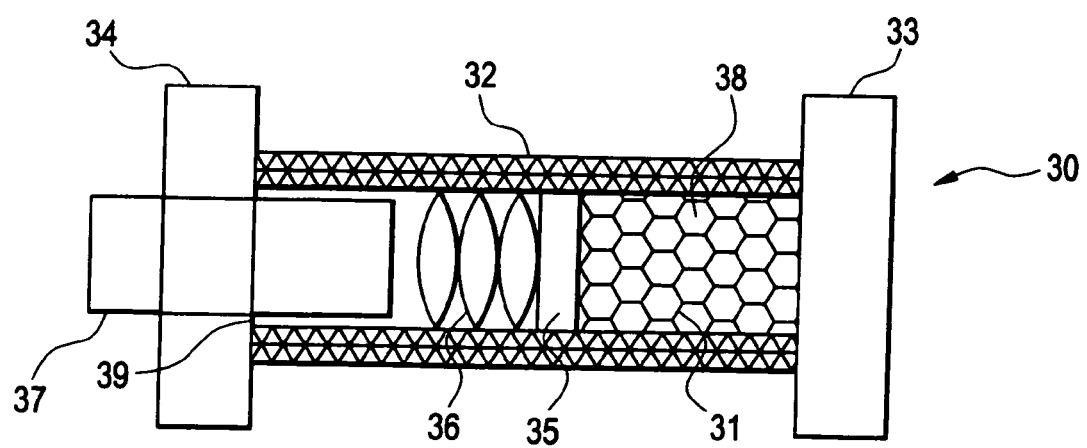
FIG. 3 provides a cross-sectional view of an exemplary column containing separation media and other components.

The chromatography columns of the present invention may further comprise a separation media suitable for use in a chromatography column. FIG. 3 provides a cross-sectional view of an exemplary column 30 containing separation media 31. As shown in FIG. 3, separation media 31 may be positioned within at least a portion of a column volume 38 enclosed by tubular wall structure 32 and flanges 33 and 34. In this particular exemplary embodiment, a piston 35 is also used to limit the position of separation media 31 within column volume 38.

Any separation media used in chromatography columns may be used in the present invention. Suitable types of separation media include, but are not limited to, rigid support media such as inorganic particles disclosed in U.S. Pat. No.

6,802,966, the disclosure of which is incorporated herein by reference in its entirety. Other suitable media include, but are not limited to, polymeric particles, organic or inorganic membranes, and inorganic or organic monoliths.

In one exemplary embodiment of the present invention, the chromatography column comprises rigid support media within a column space surrounded by the tubular wall structure. The rigid support media may comprise a plurality of organic or inorganic particles such silica, alumina, polystyrene, polymethacrylate, as those disclosed in the above-referenced patents.

4. Pistons

The chromatography columns of the present invention may further comprise a piston movable within the tubular wall structure such as exemplary piston 35 shown in FIG. 3. The piston may be used to hold packing material within the chromatography column in place. The piston moves up or down in the inner tube to compensate for changes in the volume of the packing materials that may occur from time to time. A description of chromatography columns utilizing a piston, such as exemplary piston 35 shown in FIG. 3, is disclosed in U.S. Pat. No. 5,951,873, the disclosure of which is incorporated herein by reference in its entirety.

5. Springs

The chromatography columns of the present invention may further comprise one or more springs such as springs 36 positioned within tubular wall structure 32 of exemplary column 30 shown in FIG. 3. Springs 36 may be used to move piston 35 within tubular wall structure 32 to compensate for changes in the volume of the packing material that may occur from time to time, for example, due to particle swelling or shrinking or rearrangement of the packed bed. A description of chromatography columns utilizing a spring assembly, such as spring 36 shown in FIG. 3, is disclosed in U.S. Pat. No. 5,951,873, the disclosure of which is incorporated herein by reference in its entirety.

6. Threaded Spacer

The chromatography columns of the present invention may further comprise a threaded spacer such as exemplary spacer 37 shown in FIG. 3. Spacer 37 is positioned within end 39 of tubular wall structure 32 through flange 34 of exemplary column 30. Spacer 37 may be used to compress spring 36 so as to apply pressure against piston 35 within tubular wall structure 32. Spacer 37 may be used to secure the interior components (e.g., guide tube, piston, spring washers and separation media) within a column. A description of chromatography columns utilizing a threaded spacer, such as exemplary spacer 37 shown in FIG. 3, is disclosed in U.S. Pat. No. 5,951,873 (see upper spring engaging member 56 in the '873 patent), the disclosure of which is incorporated herein by reference in its entirety.

B. Chromatography Column Configurations

The chromatography columns of the present invention may have a variety of sizes, shapes, and configurations as described below.

1. Tubular Wall Structure Cross-Sectional Shape

As shown in exemplary chromatography column 10 shown in FIGS. 1-2, columns of the present invention have a column inlet (e.g., column inlet 14) at a first end (e.g., first end 11) of the column and a column outlet (e.g., column outlet 15) at the second end (e.g., second end 12) of the column. The column inlet has an inlet cross-sectional flow area within a plane that is perpendicular to a length of the column, while the column outlet has an outlet cross-sectional flow area that is also within a plane perpendicular to a length of the column. The tubular wall structure also has a tubular cross-sectional flow area within a plane perpendicular to the length of the column at numerous points along the length of the tubular wall structure between the column inlet and the column outlet.

In one exemplary embodiment of the present invention, the tubular cross-sectional flow area is substantially equal to the inlet cross-sectional flow area, the outlet cross-sectional flow area, or both. In a further exemplary embodiment of the present invention, the tubular cross-sectional flow area is substantially equal to both the inlet cross-sectional flow area and the outlet cross-sectional flow area.

Each of the tubular cross-sectional flow area, the inlet cross-sectional flow area and the outlet cross-sectional flow area may have any desired cross-sectional configuration. Suitable cross-sectional configurations include, but are not limited to, circular, rectangular, square, pentagon, triangular, and hexagonal cross-sectional configurations. In one desired embodiment, each of the tubular cross-sectional flow area, the inlet cross-sectional flow area, and the outlet cross-sectional flow area has a circular cross-sectional flow area.

2. Column Dimensions

The chromatography columns of the present invention may have a variety of sizes depending on the use of the chromatography column. For example, chromatography columns of the present invention may have any height (also referred to herein as the column length), although columns typically have an overall height of up to about 3 meters (m). In some embodiments, chromatography columns of the present invention have a height (or length) ranging from about 50 mm to about 1.0 m.

Chromatography columns of the present invention may also have a tubular wall structure overall thickness that varies depending on the requirements of the column (e.g., the pressure capacity). Typically, chromatography columns of the present invention have a tubular wall structure overall thickness of up to about 500 mm. In some embodiments, chromatography columns of the present invention have a tubular wall structure overall thickness ranging from about 10 mm to about 200 mm.

As described above, chromatography columns of the present invention have a tubular cross-sectional flow area, an inlet cross-sectional flow area, and an outlet cross-sectional flow area. Each of the tubular cross-sectional flow area, the inlet cross-sectional flow area, and the outlet cross-sectional flow area may vary in size depending on the use of a given column. Typically, each of the tubular cross-sectional flow area, the inlet cross-sectional flow area, and the outlet cross-sectional flow area is independently up to about 650,000 $mm^2$. In some embodiments, each of the tubular cross-sectional flow area, the inlet cross-sectional flow area, and the outlet cross-sectional flow area independently ranges from about 40 $mm^2$ to about 150,000 $mm^2$.

3. Pressure Capacity

Chromatography columns of the present invention may be constructed from the above-referenced materials in order to withstand an internal pressure that varies depending on the end use of a given column. Typically, chromatography columns of the present invention are constructed to have a pressure capacity of up to about 15,000 psig. In some embodiments, chromatography columns of the present invention are constructed to have a pressure capacity ranging from about 500 to about 5,000 psig.

II. Methods of Making Chromatography Columns

The present invention is also directed to methods of making chromatography columns having at least one fiber-reinforced layer. In one exemplary method, the method of making a chromatography column comprises forming a first sleeve comprising an inert material, and surrounding an outer surface of the first sleeve with a fiber-reinforced layer. Such a process may be described with reference to FIG. 4.

Figure 4:
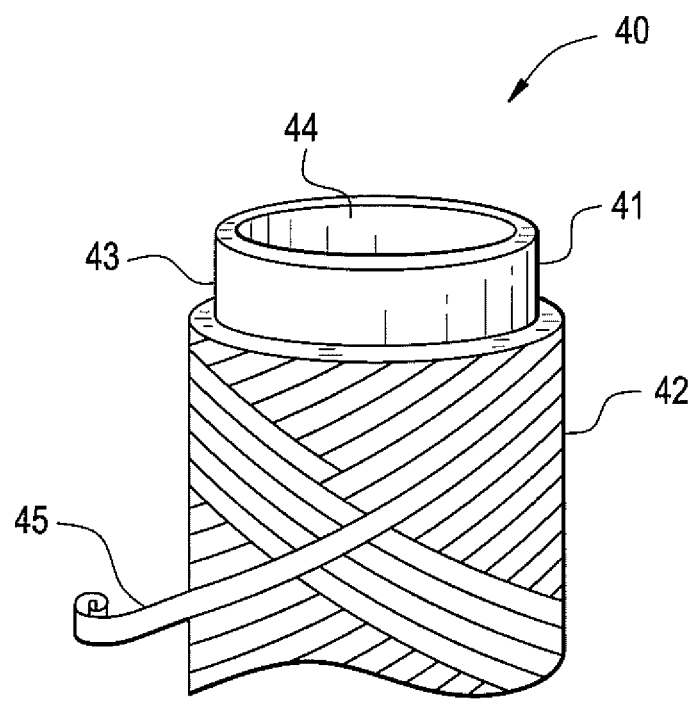
FIG. 4 depicts an exemplary chromatography column of the present invention during a manufacturing step.

As shown in FIG. 4, exemplary chromatography column 40 comprises a preformed first sleeve 41 comprising an inert material, such as aluminum, having an inner surface 44 and an outer sleeve surface 43. An exemplary fiber-reinforced tape (e.g., tape of unidirectional fibers) or prepreg 45 may be wound onto outer sleeve surface 43 of first sleeve 41. Exemplary fiber-reinforced tape or prepreg 45 may be wound onto outer sleeve surface 43 to form a fiber-reinforced resin layer 42 having a desired layer thickness so as to provide a desired degree of structural strength to exemplary chromatography column 40. Desirably, the outer wall surface of the resulting tubular wall structure is a continuous surface that extends around an outer periphery of the tubular wall structure (as shown in exemplary chromatography column 10 shown in FIG. 1 and exemplary chromatography column 40 shown in FIG. 4).

In one exemplary embodiment, preformed first sleeve 41 comprises a stainless steel sleeve, and a surface of fiber-reinforced layer 42 is in direct contact with outer sleeve surface 43. In this exemplary embodiment, an outer portion of preformed first sleeve 41 forms an inner wall surface of exemplary chromatography column 40.

Although not shown in FIG. 4, preformed first sleeve 41 could further comprise flange portions on opposite ends of preformed first sleeve 41 (such as flanges 16 and 17 of exemplary chromatography column 10 shown in FIG. 1) with the flange portions forming the first end and second end of the resulting tubular wall structure.

In an alternative embodiment, the method of making a chromatography column may comprise forming a fiber-reinforced layer over a temporary mandrel or sleeve, and subsequently removing the temporary mandrel or sleeve to provide a fiber-reinforced layer. In this embodiment, additional layers may be combined with the fiber-reinforced layer by a variety of process steps. Suitable process steps may include, but are not limited to, chemical or vapor deposition of a material onto a surface of the fiber-reinforced layer; any solution coating step for depositing a material onto a surface of the fiber-reinforced layer; and forming an inner or outer sleeve in a separate step and subsequently combining the inner or outer sleeve with the fiber-reinforced layer.

In yet a further alternative embodiment, the method of making a chromatography column may comprise forming a fiber-reinforced layer via a molding step or other thermoforming step. The fiber-reinforced layer may be formed separately in a molding step or formed simultaneously with one or more additional layers during a single molding step.

Other methods of forming the tubular wall structure of the chromatography columns of the present invention may comprise one or more method steps for forming fiber-reinforced composite materials as disclosed in U.S. Pat. Nos. 5,936,861; 5,468,358; 4,655,384; 4,305,449; 5,589,115; 5,436,042; 5,009,823; 4,927,345; and 4,357,305, the subject matter of all of which is incorporated herein by reference in its entirety.

In any of the above-described methods of making a chromatography column, the methods may include any number of additional steps. Suitable additional steps may include, but are not limited to, subjecting the fiber-reinforced layer and any additional layers to an autofrettage process step; testing the pressure capacity of the resulting chromatography column; surface treating or finishing the inner wall surface of the column to provide a desired surface smoothness thereon; sealing one end of the column; at least partially filling a column cavity of the column with a rigid support material, such as any of the above-described rigid support materials; at least partially filling the column cavity of the column with a first buffer solution to encapsulate the rigid support material; inserting a piston, spring and/or threaded rod into the chromatography column to engage, and/or compress and/or retain the rigid support material within a desired area of the column; and sealing the opposite end of the column. The chromatography column may be stored for future use or may be subsequently connected to an apparatus comprising one or more apparatus components.

III. Methods of Using Chromatography Columns

The present invention is further directed to methods of using chromatography columns having at least one fiber-reinforced resin layer. In one exemplary embodiment of the present invention, the method of using a chromatography column comprises a method of analyzing a test sample that potentially contains at least one analyte. In this exemplary method, the method comprises the step of introducing a test sample into a chromatography column containing a rigid support media, wherein the chromatography column comprises a tubular wall structure comprising a fiber-reinforced resin layer as described above. The rigid support media may comprise a plurality of inorganic particles such as those disclosed in U.S. Pat. No. 6,802,966, the disclosure of which is incorporated herein by reference in its entirety. Other rigid support materials may comprise organic particles, inorganic or organic monoliths or membranes.

The method of analyzing a test sample may further comprise one or more of the following steps: allowing the test sample to come into contact with the rigid support; rinsing the rigid support to wash away any test sample components other than the one or more analytes; introducing an eluent solution into the column so that the eluent solution comes into contact with the one or more analytes bound to the rigid support; and allowing the eluent solution to remain in contact with the rigid support for a period of time so as to form an eluent sample. Typically, the eluent solution remains in contact with the rigid support for a period of time ranging from about 5 minutes to about 15 minutes.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE 1

Preparation of a Chromatography Column

A sleeve comprising type 316 stainless steel was formed during a die casting process. The resulting sleeve had an overall length of 1.0 m, a circular cross-sectional configuration with an inner diameter of 25 mm, a sleeve wall thickness of 2.0 mm, and flanges on each end of the sleeve. Each flange extended outward from the sleeve, had a circular configuration with an outer diameter of 100 mm, and had a flange wall thickness of 71 mm. The sleeve was positioned on a winding apparatus capable of rotating the sleeve along an axis extending along a length of the sleeve through a central portion of the aluminum sleeve.

A carbon fiber tape (designated P3052S-10 from Toray Industries, Inc. (Tokyo, JP)) comprising T700SC carbon fiber tow (67 wt %) embedded within an epoxy resin system (33 wt %) was wound directly onto the aluminum sleeve so as to cover an outer surface of the aluminum sleeve extending from a first flange to a second flange. The carbon fiber tape was wound onto the aluminum sleeve so as to form a fiber-reinforced resin layer having a thickness of about 4.0 mm. The composite sleeve was then heat cured in an oven at about 190° C.

The resulting column had an overall wall thickness of 6.0 mm, and a pressure capacity of about 5000 psig.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A chromatography column comprising a tubular wall structure having a first end, a second end, an inner wall surface facing an interior of the tubular wall structure; and
   an outer wall surface, said tubular wall structure comprising a fiber-reinforced layer wherein the inner wall surface comprises a metal; and
   wherein the column is capable of withstanding a pressure of up to about 15,000 psig.

2. The column of claim 1, wherein the metal comprises aluminum or stainless steel.

3. The column of claim 1, further comprising:
   a column inlet at the first end of the tubular wall structure, said column inlet having an inlet cross-sectional flow area; and
   a column outlet at the second end of the tubular wall structure, said column outlet having an outlet cross-sectional flow area;
   wherein the tubular wall structure has a tubular cross-sectional flow area between the column inlet and the column outlet, said tubular cross-sectional flow area being substantially equal to the inlet cross-sectional flow area, the outlet cross-sectional flow area, or both.

4. The column of claim 3, wherein the tubular cross-sectional flow area is substantially equal to both the inlet cross-sectional flow area and the outlet cross-sectional flow area.

5. The column of claim 4, wherein each of the tubular cross-sectional flow area, the inlet cross-sectional flow area, and the outlet cross-sectional flow area has a circular cross-sectional flow area.

6. The column of claim 1, wherein the tubular wall structure comprises an outer fiber-reinforced layer and an inner metal layer, wherein an outer portion of said inner metal layer forms the inner wall surface.

7. The column of claim 6, wherein the inner metal layer comprises aluminum or stainless steel.

8. The column of claim 6, wherein a surface of the outer fiber-reinforced layer is in direct contact with a surface of the inner metal layer.

9. The column of claim 1, wherein the tubular wall structure comprises an outer sleeve of fiber-reinforced material and an inner sleeve of metal, wherein an outer portion of said inner sleeve forms the inner wall surface.

10. The column of claim 9, wherein the inner sleeve comprises flange portions on opposite ends of the inner sleeve, said flange portions forming the first end and second end of the tubular wall structure.

11. The column of claim 1, wherein the outer wall surface of the tubular wall structure is a continuous surface that extends around an outer periphery of the tubular wall structure.

12. The column of claim 1, wherein the fiber-reinforced layer comprises fibers embedded in a thermoplastic or thermoset resin, a ceramic matrix material, a metal or metal oxide matrix material, or a carbon matrix material; and said fibers comprise carbon fibers, aramid fibers, glass fibers, polybenzoxazole (PBO) fibers, or a combination thereof.

13. The column of claim 1, wherein the fiber-reinforced layer comprises an epoxy resin.

14. The column of claim 1, further comprising rigid support media within a column space surrounded by the tubular wall structure.

15. The column of claim 14, wherein the rigid support media comprises a plurality of inorganic particles.

16. A method of treating a test sample that potentially contains at least one analyte, said method comprising the steps of:
   introducing the test sample into the column of claim 14.

17. A chromatography column comprising:
   a column inlet at a first end of the column, said column inlet having an inlet cross-sectional flow area;
   a column outlet at a second end of the column opposite the first end, said column outlet having an outlet cross-sectional flow area; and
   a tubular wall structure extending between the column inlet and the column outlet, said tubular wall structure having a tubular cross-sectional flow area that is substantially constant along a length of the tubular wall structure and is substantially equal to the inlet cross-sectional flow area, the outlet cross-sectional flow area, or both;
   wherein said tubular wall structure comprises:
      an outer fiber-reinforced layer; and
      an inner metal layer; and
   wherein the chromatography column is capable of withstanding pressures of up to about 15,000 psig.

* * * * *